United States Patent [19]

Greczyn et al.

[11] Patent Number: 5,302,381
[45] Date of Patent: Apr. 12, 1994

[54] LOW RESIDUE ANTIPERSPIRANT STICKS

[75] Inventors: Wendy R. Greczyn, Randolph; Linda J. Lancaster, Old Bridge; Richard T. Murphy, Belle Mead, all of N.J.

[73] Assignee: Church & Dwight Co., Inc., Princeton, N.J.

[21] Appl. No.: 937,525

[22] Filed: Aug. 27, 1992

Related U.S. Application Data

[63] Continuation-in-part of Ser. No. 854,209, Mar. 20, 1992, Pat. No. 5,254,332.

[51] Int. Cl.$^5$ .................. A61K 7/32; A61K 7/34; A61K 7/36; A61K 7/38
[52] U.S. Cl. ............... 424/66; 424/DIG. 5; 424/65; 424/67; 424/68
[58] Field of Search ............. 424/66, 68, DIG. 5

[56] References Cited

U.S. PATENT DOCUMENTS

| | | | |
|---|---|---|---|
| 4,414,200 | 11/1983 | Murphy et al. | 424/68 |
| 4,425,328 | 1/1984 | Nabial | 424/68 |
| 4,664,909 | 5/1987 | Marschner | 424/DIG. 5 |
| 4,725,432 | 2/1988 | May | 424/65 |
| 4,822,603 | 4/1989 | Farris et al. | 424/DIG. 5 |
| 4,937,069 | 6/1990 | Shin | 424/68 |
| 4,944,937 | 7/1990 | McCall | 424/68 |

Primary Examiner—Dale R. Ore
Attorney, Agent, or Firm—Charles B. Barris

[57] ABSTRACT

This invention relates to an antiperspirant stick which provides the user with excellent antiperspirant/deodorant efficacy, reduced residue and high temperature stability, which comprises: (a) from about 10 to 70 percent by weight of a volatile silicone oil; (b) from about 1.5 to 30 percent by weight of a water-insoluble liquid emollient, characterized in that the weight ratio of volatile silicone oil to water-insoluble liquid emollient is greater than about 2.5:1.0; (c) from about 12 to 20 percent by weight of a low melting point wax; (d) from about 1.0 to 15 percent by weight of a coupling agent; (e) from about 0.50 to 3.0 percent by weight of a surface active agent; (f) from about 18 to 30 percent by weight of an antiperspirant active material; and (g) from about 0.05 to 30 percent by weight of a deodorant active material.

26 Claims, No Drawings

LOW RESIDUE ANTIPERSPIRANT STICKS

CROSS REFEENCE TO RELATED APPLICATIONS

The subject matter of the present patent application is a continuation-in-part of U.S. patent application Ser. No. 07/854,209 filed Mar. 20, 1992, now U.S. Pat. No. 5,254,332.

TECHNICAL FIELD

This invention relates to cosmetic compositions of matter in stick form, particularly to antiperspirant sticks which also provide deodorization efficacy.

More particularly, the present invention relates to antiperspirant sticks which provide the user with smooth application, excellent antiperspirant efficacy plus deodorization, reduced residue when the composition is first applied to the skin, reduced residue on the skin after dry down, high temperature stability, and excellent cosmetics and aesthetics.

BACKGROUND OF THE INVENTION

Antiperspirants combat axillary odors by inhibiting perspiration through the action of astringent salts such as aluminum and zinc salts, but may be irritating to a considerable number of users. On the other hand, deodorants neutralize the objectionable odors resulting from the degradation of the components of sweat due to chemical and microbial attack into malodorous fatty acids. Deodorants do not inhibit sweating but rather neutralize the malodorous degradation products of sweat, either by their own odorous properties, or by the inhibition of the decomposition action of microbial action on the fats in the sweat residues, or by reaction with the malodorous fatty acids or by any combination of these mechanisms.

Numerous stick antiperspirant compositions are known in the art. Those skilled in the art have found that anhydrous antiperspirant stick systems are more advantageous to market and have good consumer acceptance primarily due to the ease of application to the skin, good cosmetic aesthetics and an acceptable degree of effectiveness. Previous to the development of anhydrous stick systems, numerous water based systems were developed in which the active astringent salts were solubilized in a thickened or gelled composition. This is exemplified in U.S. Pat. Nos. 2,732,327, 2,857,315, 3,255,082, and 3,928,557. The water based systems are difficult to apply to the skin and their consistency and effectiveness are questionable.

Many anhydrous stick compositions have been described in the literature which attempt to improve the delivery and the effectiveness of their antiperspirant and deodorant characteristics. For example, antiperspirant stick systems consisting of low molecular weight monohydric alcohols in conjunction with polyhydric alcohols, as described in U.S. Pat. No. 4,137,306 have the advantage of quicker drying rates, but the residue of the polyhydric alcohols in combination with the astringent salts produces a high degree of tack and their effectiveness is limited to the type and amount of astringent salts that could be incorporated therein.

Anhydrous stick compositions that suspend the aluminum salt in a hydrophobic matrix, as described in U.S. Pat. No. 4,049,792, make use of waxy materials and long chain fatty esters to form a stick that delivers the active astringent salts to the skin. Preparations made by these teachings are rather greasy and they envelop the active astringent salt for long periods of time preventing their maximum performance. To alleviate this inherent negative characteristic, volatile silicone fluids replaced the lesser volatile long chain fatty esters as described by U.S. Pat. No. 4,126,679. This patent teaches the advantage of incorporating a volatile, non-staining liquid such as cyclic dimethylpolysiloxanes, referred to as volatile silicones, in combination with various types of waxes as a carrier for the active astringent salts in an antiperspirant stick composition. Similar antiperspirant stick compositions containing volatile silicones are described in U.S. Pat. Nos. 4,511,554, 4,980,156 and 4,985,238.

Although the volatile silicone based antiperspirant stick compositions are effective and highly aesthetic, they may contain up to 80% by weight of volatile silicone. While the use of such large amounts of volatile silicone make preparations thusly prepared more stable, they may be brittle and hard and, more importantly, they tend to leave an unsightly white chalky residue on the skin after application. This residue is not only aesthetically displeasing to the user, but can also soil clothing. In an effort to alleviate this problem, U.S. Pat. No. 4,985,238 discloses that when certain non-volatile paraffinic hydrocarbon fluids, such as mineral oils or branched chain $C_{16}$–$C_{68}$ hydrocarbons, are incorporated into water-free suspensoid antiperspirant stick compositions, these compositions exhibit antiperspirant efficacy and aesthetics, while leaving reduced visible residue on the skin of the user.

The compositions of U.S. Pat. No. 4,985,238 or any of the related art, however, do not contemplate the use of relatively large amounts of a deodorant active material, such as a carbonate or a bicarbonate, in conjunction with the active astringent salts.

Sodium bicarbonate has long been recognized for its deodorant properties, and has commonly been used as a household deodorant. Plain powdered sodium bicarbonate or sodium bicarbonate diluted with talc, cornstarch, rice-flour, or other filler has been used as an underarm deodorant as disclosed in U.S. Pat. No. 4,382,079.

However, the development of a practical and effective antiperspirant composition in stick form which is also capable of deodorization and, which is capable of consumer acceptability, presents many considerations which are unique. Because sodium and potassium bicarbonate have only limited solubility in water, alcohol and other solvents, the preparation of a composition suitable for dispensing in stick form has been an exceedingly difficult and perplexing problem. In addition to the problem of limited solubility of the sodium bicarbonate; its incompatibility with the active astringent salts and with other ingredients of conventional stick compositions; the dimensional stability of the stick containing sodium bicarbonate; its aesthetic appearance and its "feel" on the skin, are just a few of the additional problems encountered in the preparation of a low residue antiperspirant/deodorant stick.

While antiperspirant sticks are old, as evidenced by the above patents, none of these publications suggests the criticality of the specific combination of components described by the present invention. This combination of components gives antiperspirant sticks which are both highly efficacious and cosmetically pleasing.

It is therefore an object of the present invention to provide cosmetic sticks which have excellent cosmetic properties (e.g., ease of application to skin, "glide", a low visible residue) and are easy to manufacture. A further object of the present invention is to provide cosmetic sticks which very effectively deliver water-soluble active materials, particularly deodorant and/or antiperspirant active materials, to the skin. A still further object of the present invention is to provide cosmetic compositions which feel dry; do not feel greasy or gritty; go on cleanly and evenly; remain evenly dispersed with no visible cakey, chalky residue after application; and appear uniformly opaque and non-gritty. An object of the present invention is also to provide methods for treating or preventing malodor associated with human perspiration, especially underarm odor.

It has been surprisingly discovered that the above objectives can be realized by formulating a stick comprising the ingredients described hereinafter.

SUMMARY OF THE INVENTION

This invention relates to an antiperspirant stick which provides the user with excellent antiperspirant/deodorant efficacy, reduced residue and high temperature stability, which comprises (a) from about 10 to 70 percent by weight of a volatile silicone oil;

(b) from about 1.5 to 30 percent by weight of a water-insoluble liquid emollient;

characterized in that the weight ratio of volatile silicone oil to water-insoluble liquid emollient is greater than about 2.5:1.0.

(c) from about 12 to 20 percent by weight of a low melting point wax;

(d) from about 1.0 to 15 percent by weight of a coupling agent;

(e) from about 0.50 to 3.0 percent by weight of a surface active agent;

(f) from about 18 to 30 percent by weight of an antiperspirant active material; and (g) from about 0.05 to 30 percent by weight of a deodorant active material.

It is desirable to use a weight ratio of volatile silicone oil to water-insoluble liquid emollient of from about 5.0:1 to 25.0:1, preferably, from about 10.0:1 to 20.0:1, for example, about 13.0:1 to 15.0:1.

The present invention also relates to methods for treating or preventing malodor associated with human perspiration, especially underarm odor. These methods comprise applying to the skin of a human a safe and effective amount of an antiperspirant/deodorant cosmetic stick composition of the present invention.

DETAILED DESCRIPTION OF THE INVENTION

Antiperspirant Stick Compositions

The antiperspirant/deodorant stick compositions of the present invention comprise the following components: (a) volatile silicone oil; (b) water-insoluble emollient; (c) low melting point wax; (d) coupling agent; (e) surface active agent; (f) antiperspirant active; and (g) deodorant active.

The specific components to be included in the stick products of the present invention, and their levels, are selected in order to produce a stick of desired hardness so as to maintain dimensional stability while depositing a suitable amount of the antiperspirant and the deodorant active onto the skin during normal use. These components, and the weight percentages for these components, are described in detail immediately hereinafter.

(a) Volatile Silicone Oil

The compositions of the present invention essentially comprise at least one volatile silicone oil in an amount in total of from about 10 to 70 percent by weight, preferably, from about 25 to 50 percent by weight of the total composition. The term "volatile", as used herein, refers to those materials which have a measurable vapor pressure at ambient temperature and is not dimethicone copolyol.

The volatile silicone oils useful in the antiperspirant stick compositions of the present invention are preferably cyclic or linear polydimethylsiloxanes containing from about 3 to 9, preferably from about 3 to 6, silicon atoms. The following formula illustrates the cyclic volatile polydimethylsiloxanes useful in the antiperspirant stick compositions disclosed herein have the following general formula:

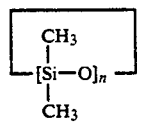

wherein n equals from about 3 to 7.

The linear polydimethylsiloxanes contain from about 3 to 9 silicon atoms per molecule and have the following general formula:

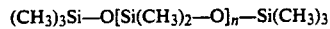

wherein n equals from about 1 to 7.

The linear volatile silicone materials generally have viscosities of less than about 5 centistokes at 250° C. While the cyclic materials have viscosities of less than about 10 centistokes.

Typical of the volatile silicones that may be employed herein is a material that is referred to as Cyclomethicone. This is a cyclic dimethylpolysiloxane that conforms to the above formula wherein n averages between 3 and 6. A number of cyclomethicone products are available commercially. These include Dow Corning 245 Fluid (Dow Corning) and a host of others. See for example *CTFA Cosmetic Ingredient Dictionary*, Third Edition, (Estrin et al., Editors; The Cosmetic, Toiletry and Fragrance Association, Inc.; 1982), page 60, under the entry "Cyclomethicone" the disclosure of which is incorporated herein by reference in its entirety.

(b) Water-Insoluble Liquid Emollient

The compositions of the present invention also essentially comprise at least one water-insoluble emollient in an amount in total of from about 1.5 to 30 percent by weight, preferably, from about 2 to 20 percent by weight of the total composition. The term "water-insoluble liquid emollient", as used herein, refers to a water-insoluble material which is in the liquid state at ambient temperature (about 22 degrees C.) and has a water solubility of less than about 1% at 25 degrees C. From these liquids which are organic in nature a group is selected which has a low degree of irritation and toxicity, that is generally considered safe for topical use, that provides a softening or soothing effect on surface skin tissue and is referred to herein as the "water-insoluble liquid emollients" of the present compositions. Preferred water-insoluble liquid emollients include fatty acids such as oleic and recinoleic; fatty alcohols such as oleyl, lauryl, and hexadecyl; esters such as diisopropyl adipate, benzoic acid esters of $C_9$–$C_{15}$ alcohols, and isononyl isononanoate; alkanes such as mineral oil; silicones such as dimethyl polysiloxane; and cyclic dimethyl polysiloxane and ethers such as polyoxypropylene butyl ethers and polyoxypropylene cetyl ethers. The preferred water-insoluble liquid emollients are: diisopropyl adipate, 2-ethylhexyl palmitate, dimethylpolysiloxane 50 cst. and polyoxypropylene (14) butyl ether.

The most preferred water-insoluble liquid emollient is diisopropyl adipate which is available commercially, e.g., Ceraphyl 230 (Van Dyk), as well as many other similar products, are found in *CTFA Cosmetic Ingredient Dictionary*, Third Edition, (Estrin et al., Editors; The Cosmetic, Toiletry and Fragrance Association, Inc.; 1982), page 82, under the entry "Diisopropyl Adipate" the disclosure of which is incorporated herein by reference in its entirety.

(c) Low Melting Point Waxes

Waxes used in the present compositions are usually referred to as substances that are plastic solids at ambient temperature and, on being subjected to moderate elevated temperatures, become low viscosity liquids. Because they are plastic, waxes usually deform under pressure without application of heat. The chemical composition of waxes is complex and usually contains a broad spectrum of molecular weight species and reactive functional groups. For this reason the present invention should not be limited only to the waxes mentioned in the present specification and claims.

The antiperspirant sticks of the present invention contain one or more low melting wax-like materials in an amount in total of from about 12 to 20 percent by weight, preferably, from about 15 to 19 percent by weight based on the total weight of the composition. Such wax-like materials are characterized by having a low melting point, i.e., having a melting point of from about 37–40 degrees C. to about 65–75 degrees C. Such materials are well known in the art and include fatty acids, fatty alcohols, fatty acid esters, and fatty acid amides, having fatty chains of from about 8 to about 30, preferably from about 12 to about 18, carbon atoms. Preferred low melting point waxes include cetyl alcohol, palmitic acid, myristyl alcohol, stearyl alcohol, paraffin, and mixtures thereof. Stearyl alcohol, cetyl alcohol, and mixtures thereof are particularly preferred.

The most preferred low melting wax is stearyl alcohol. A number of stearyl alcohol products are available commercially. These include CO 1895 (P&G) as well as many others. Additional examples can be found in *CTFA Cosmetic Ingredient Dictionary*, Third Edition, (Estrin et al., Editors; The Cosmetic, Toiletry and Fragrance Association, Inc.; 1982), page 304, under the entry "Stearyl Alcohol" the disclosure of which is incorporated herein by reference in its entirety.

The low melting point waxes described above can be used with other adjunct water-insoluble waxes which are described more fully hereinlater to provide emolliency and also to control the rate of product depositing on the skin. One skilled in the art will be able to adjust the cosmetic aesthetics and physical structure by combining various suitable water-insoluble waxes with the water-insoluble liquid emollients.

The low melting point wax may be replaced in whole or, preferably, in part by a high melting point wax. Suitable waxes are water-insoluble waxes having a melting point of from about 65 degrees to 100 degrees C. Examples of such suitable waxes are beeswax, spermaceti, carnauba, bayberry, candelilla, montan, ozokerite, ceresin, paraffin, castor wax, synthetic waxes such as Fischer-Tropsch waxes, and microcrystalline waxes and mixtures thereof. Hydrogenated castor oil (Castor wax) is a preferred high melting point wax for use herein. The present compositions may contain from about 0.5 to 5 percent by weight of this wax based on the total weight of the composition. The preferred amount of high melting point wax is from about 1 to 3 percent by weight.

The total quantity of waxy material that may be contained in the present antiperspirant stick compositions may vary somewhat. Ordinarily, this will comprise about 12 to 25 percent by weight based on the total weight of the composition. The preferred range is from about 16 to 22 percent by weight.

(d) Coupling Agent

The compositions of the present invention also essentially comprise at least one coupling agent in a total amount of from about 1.0 to 15 percent by weight, preferably, from about 2.0 to 10 percent by weight, based on the total weight of the stick composition.

The term "coupling agent", as used herein, means any compound, composition, or combination thereof which acts to bring any polar, intermediately polar and non-polar components of the present invention into a homogeneous stick composition.

Useful coupling agents include $_6$–$C_{22}$ fatty alcohols, ethoxylated derivatives of $C_4$–$C_{22}$ fatty alcohols, propoxylated derivatives of $C_4$–$C_{22}$ fatty alcohols, and mixtures thereof. More preferred are ethoxylated derivatives of $C_{10}$–$C_{20}$ fatty alcohols, propoxylated derivatives of $C_{10}$–$C_{20}$ fatty alcohols, and mixtures thereof.

The most preferred coupling agents for use herein are polypropylene glycol ("PPG") ethers of $C_4$–$C_{22}$ (preferably $C_{10}$–$C_{20}$) fatty alcohols. Examples of such materials are: PPG-5-ceteth-20, PPG-4 myristyl ether, PPG-4 lauryl ether, PPG-10 cetyl ether, PPG-3 myristyl ether, and especially PPG-14 butyl ether (Fluid AP), and mixtures thereof. Additional examples are found in *CTFA Cosmetic Ingredient Dictionary*, Third Edition (Estrin et al., Editors; The Cosmetic, Toiletry and Fragrance Association, Inc.; 1982), pages 252–260 and 494–500, the disclosures of which are incorporated herein by reference in their entirety.

(e) Surface Active Agent

It is also advantageous to incorporate one or more surface active agents in the antiperspirant/deodorant stick composition of this invention. This facilitates better contact between the antiperspirant or other active ingredients and the skin and helps to increase its activity. Moreover, it also facilitates the removal of the product while washing, bathing or showering.

The present antiperspirant/deodorant compositions contain from about 0.5 to 3.0 percent by weight, preferably, from about 1.0 to 2.0 percent by weight of the surface active agent, based on the total weight of the stick composition. Preferred surface active agents are selected from a group of non-ionic ethers and esters having a HLB greater than about 10. By way of example, mention may be made of the following: polyoxyethylene (25) stearyl alcohol, polyoxyethylene (25) stearyl ether, polyoxyethylene (150) dioleate, polyoxyethylene (40) octyl phenyl ether and polyoxyethylene (20) sorbitan tristearate.

The most preferred surface active agent is polyethylene glycol (PEG) distearate. A number of PEG distearate products are available commercially. These include PEG -12 distearate,(Mapeg 600 DS) as well as many others. Additional examples can be found in *CTFA Cosmetic Ingredient Dictionary*, Third Edition, (Estrin et al., Editors; The Cosmetic, Toiletry and Fragrance Association, Inc.; 1982), page 209, under the entry "P&G Distearate" the disclosure of which is incorporated herein by reference in its entirety.

(f) Astringent Antiperspirant Salt

The present compositions contain from about 18 to 30 percent by weight, preferably, from about 20 to 24 percent by weight, based on the total weight of the stick composition, of a particulate antiperspirant material. These weight percentages are calculated on an anhydrous metal salt basis (exclusive of glycine, the salts of glycine, or other complexing agents). The particulate antiperspirant material preferably has particle sizes ranging from about 1 to about 100 microns, more preferably from about 1 to about 50 microns. They may be impalpable or microspherical in form and, preferably, have a high bulk density (e.g., greater than about 0.7 g/cm$^3$).

Ingredients that produce a reduction in sweat in the axilla area by physiological action are hereinafter referred to herein as "active astringent antiperspirant salts" or the like. Examples of these astringent salts in the form of impalpable particles are aluminum chloride, aluminum chlorohydrates, aluminum sulfocarbolate, aluminum sulfate, aluminum-zirconium chlorohydrates, aluminum-zirconium tetrachlorohydrex gly., zinc sulfate, zinc sulfocarbolate, and zirconium chlorohydrate. The preferred astringent antiperspirant salts are the aluminum chlorohydrates and aluminum-zirconium chlorohydrates. A particularly preferred astringent active salt is aluminum zirconium tetrachlorohydrex gly. which is commercially available as Rezal 36 GP Superultrafine (Reheis).

Aluninum zirconium tetrachlorohydrex Gly. is a coordination complex of aluminum zirconium tetrachlorohydrate (q.v.) and glycine (q.v.) in which some of the water molecules normally coordinated to the metals have been displaced by the glycine. Additional examples are found in *CTFA Cosmetic Ingredient Dictionary*, Third Edition (Estrin et al., Editors; The Cosmetic, Toiletry and Fragrance Association, Inc.; 1982), page 13, the disclosure of which are incorporated herein by reference in its entirety.

(g) Deodorant Active Material

Deodorant active materials useful in the present invention are well known in the art. Such deodorant actives are usually present at levels of from about 0.05 to 30 percent by weight of the total antiperspirant stick. The specific amount of deodorant active material will vary according to the particular material employed, as is set forth below.

Preferred deodorant actives for use in the antiperspirant compositions of the present invention are carbonate and bicarbonate salts, and mixtures thereof, such as, for example, alkali metal carbonates, alkali metal bicarbonates, and ammonium and tetraalkylammonium carbonate and bicarbonate salts. More preferred are the alkali metal carbonates, and especially the alkali metal bicarbonates, such as, for example, sodium carbonate, potassium carbonate, potassium bicarbonate, and especially sodium bicarbonate, or mixtures thereof. The carbonate and bicarbonate salts typically comprise in total from about 1 to 30 percent by weight, preferably, from about 5 to 20 percent by weight of the total antiperspirant composition.

The deodorant active material incorporated into the antiperspirant stick, e.g., the alkali metal bicarbonate, preferably, sodium bicarbonate, will generally have an average particle size of from about less than 5 up to 250 microns and above. The smaller the particles, the easier it usually is to incorporate the deodorant active material into the stick composition. Further, the resultant stick affords a non-gritty, smoother feel upon application to the skin. Thus while the use of bicarbonates in the range of from about 44 to 100 microns is acceptable, the use of a superfine, e.g. micronized, bicarbonate deodorant active material having an average particle size of from about 5, or less, to 40 microns is also contemplated.

Known bacteriostats may also be added, although the bicarbonate-containing antiperspirant stick per se is effective as a deodorant without the use of added bacteriostats.

Suitable bacteriostats include bacteriostatic quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, stearyl trimethyl ammonium chloride, sodium aluminum chlorohydroxy lactate, tricetylmethyl ammonium chloride, 2,4,4'-trichloro-2'-hydroxy diphenyl ether, and zinc salts such as zinc citrate, zinc salicylate, and mixtures thereof. The preferred deodorant material is 2,4,4'-trichloro-2'-hydroxy diphenyl ether (Triclosan). These bacteriostats generally comprise from about 0.05 to 10.0 percent by weight and, preferably, about 0.08 to 3.0 percent by weight of the total stick composition.

As hereinbefore disclosed the antiperspirant/deodorant stick compositions of the present invention comprise the following essential components: (a) a volatile silicone oil; (b) a water-insoluble emollient; (c) a low melting point wax; (d) a coupling agent; (e) a surface active agent and as active ingredients (f) an antiperspirant active and (g) a deodorant active.

When employed in the amounts disclosed herein the resulting category benefits are optimized wetness protection and odor prevention. Three additional major areas of consumer appeal which distinguish the cosmetic articles of the present invention over those of the art are; smooth application wherein the product glides on very dryly and smoothly; no residue wherein there is little or no presence of residue on skin after application which translates to the undesirable white marks on clothing; and deodorization wherein the presence of a bicarbonate provides extra odor protection.

In order to attain the above advantages, it has been found that it is essential to employ a weight ratio of volatile silicone oil to water-insoluble liquid emollient which is greater than about 5.0:1.0. As supported in the Examples hereinlater presented, it is desirable to provide a weight ratio of volatile silicone oil to water-insoluble liquid emollient of greater than about 2.5:1, preferably, from about 5.0:1 to 25.0:1. It is more preferable to utilize a weight ratio of from about 10.0:1 to 20.0:1, for example, about 13.0:1 to 15.0:1.

Optional Components

The compositions of the present invention may also contain optional components which modify the physical characteristics of the compositions or serve as "active" components when deposited on the skin in addition to the antiperspirant and/or deodorant active material. Examples of such additional actives include bacteriostats and fungistats.

The specific non-active optional components that may be useful will depend upon the characteristics desired for the particular stick composition. Such components include, for example, hardeners, strengtheners, chelating agents, emollients, colorants, perfumes, and emulsifiers.

Although the present compositions may also contain fillers and particulate materials (such as talc) and suspending materials such as silica (fumed and non-fumed) other than the antiperspirant and deodorant actives described above, such particulates may adversely affect the perceived low residue benefits of the present invention. As used herein, "particulate materials" are those materials that neither dissolve in the composition components, nor melt during manufacture of the stick. Preferably, the compositions of the present invention contain a total level of particulate materials, other than the antiperspirant materials, of less than about 4 percent by weight and, more preferably, the present compositions contain less than about 3 percent by weight of the total composition of particulate materials other than the particulate antiperspirant and deodorant material.

As mentioned, a preferred suspending material useful herein is finely divided silica, or "colloidal silica", which is comprised of micron to sub-micron sized silica particulates, with high surface areas (preferably greater than about 100 square meters per gram of material). Preferably, the colloidal silica material is less than about 1 micron in size. Also preferably, the silica material used in the present compositions is a fumed silica.

Fumed silicas can generally be described as fluffy, white, superfine powders of extremely low bulk density but having high surface areas. These fumed silicas are typically made by a vapor phase process that produces colloidal silica by the hydrolysis of silicon tetrachloridce at a very high temperature. These materials typically consist of about 99.8% silicon dioxide by weight (on a moisture free basis), existing in three dimensional branched chain aggregates, with a surface that is hydrophilic and capable of hydrogen bonding. Such silicas have surface areas ranging from about 2.5 to about 1,200 square meters per gram.

Colloidal silica materials among those useful herein are available from a variety of sources, including Syloid silicas (manufactured by Davison Chemical Division of W. R. Grace), Cab-O-Sil (manufactured by Cabot Corporation), and Aerosil (manufactured by Degussa A. G.). Aerosil is the preferred commercially available colloidal silica useful herein. Additional examples are found in *CTFA Cosmetic Ingredient Dictionary*, Third Edition (Estrin et al., Editors; The Cosmetic, Toiletry and Fragrance Association, Inc.; 1982) page 278 under the entry "Silica", the disclosure of which is incorporated herein by reference in its entirety.

The specific essential and optional materials and their levels to be included in specific stick compositions of the present invention are, in part, selected in order to produce a stick of desired hardness so as to maintain dimensional stability while depositing a suitable amount of active materials on the skin during normal use. Hardness of sticks can be determined in a variety of methods, including American Society for Testing Materials (ASTM) Method D5. This method involves the use of a needle or polished cone of particular weight and dimension, which is allowed to travel downward through the stick material for a predetermined period of time. The distance traveled by the needle or cone is a relative measure of the stick hardness. Utilizing Method D5, with a penetration needle (Catalog No. 73520; sold by Precision Scientific, Inc.) weighing 2.5 grams, and a Precision Penetrometer Catalog No. 73510 (also sold by Precision Scientific, Inc.), the cosmetic sticks of the present invention preferably yield a penetration value of from about 4 to about 12 millimeters, more preferably from about 7 to about 9 millimeters, over a period of 5 seconds. These values represent an average penetration for sticks within a given production batch, since such penetration values may vary from stick to stick within the batch.

The present invention also provides methods for treating or preventing perspiration and malodor associated with human underarm perspiration. These methods comprise applying to the skin of a human a safe and effective amount of the antiperspirant stick of the present invention. The term "a safe and effective amount", as used herein, is an amount which is effective in eliminating or substantially reducing perspiration and malodor associated with human underarm perspiration while being safe for human use at a reasonable risk/benefit ratio.

The following examples further describe and demonstrate embodiments within the scope of the present invention. These examples are solely for the purpose of illustration and are not to be construed as limitations of the present invention as many variations are possible without departing from the spirit or scope thereof.

EXAMPLE I

Bicarbonate-Containing Antiperspirant Stick

A sodium bicarbonate-containing antiperspirant stick of the present invention is prepared comprising the following ingredients:

| INGREDIENTS | | | |
|---|---|---|---|
| Supplier | Trade Name | CTFA Name | Weight Percent |
| Dow | Dow 245 | Cyclomethicone | 42.25 |
| Van Dyk | Ceraphyl 230 | Diisopropyl adipate | 3.00 |
| P & G | C01895 | Stearyl alcohol | 17.00 |
| CasChem | Castorwax MP-70 | Hydrogenated castor oil | 3.00 |
| Cabot | Cab-O-Sil M-5 | Fumed silica | 0.75 |
| Mazer | Mapeg 600 DS | PEG −12 distearate | 2.00 |
| Reheis | Rezal 36GP SUF | Aluminum zirconium tetrachlorohydrex glycine | 24.00 |
| Vista | Alfol 20+ Alcohol | Eicosanol | 0.50 |
| Church & Dwight | Baking Soda 3DC | Sodium Bicarbonate 3DC | 5.00 |
| Amerchol | Fluid AP | PPG 14 butyl Ether | 2.00 |
| — | Fragrance | | 0.50 |

| INGREDIENTS | | | |
|---|---|---|---|
| Supplier | Trade Name | CTFA Name | Weight Percent |
| | | | 100.00 |

The ratio of Cyclomethicone to Diisopropyl adipate was about 14:1.

This antiperspirant stick composition is prepared on a 1.0 kilo scale as follows: First, the liquid and wax ingredients were mixed and heated to melt the waxes. The powdered ingredients, except for the bicarbonate, were then added to the foregoing, mixed and homogenized. The bicarbonate was then added and mixed and subsequently homogenized again. The final product was filled into sample bottom fill and top fill containers.

Samples of the above formulation were subjected to an efficacy screening test. In such test the antiperspirant deodorant stick composition was applied to the underarm skin of a human to effectively reduce perspiration and prevent underarm odor resulting from perspiration. The composition applied smoothly and during application to the skin had a dry feel, and did not feel greasy or gritty. The composition provided a clean coat of antiperspirant and deodorant protection and left essentially no residue.

Such efficacy testing showed that this formulation meets the efficacy requirements set forth in the monograph dated Aug. 20, 1982 relating to "Antiperspirant Drug Products for Over-the-Counter Human Use" published by the Department of Health and Human Services, Food and Drug Administration.

The tests indicated that one hour after treatment of thirty-three panelists, there was a cumulative average sweat reduction of 45% and thirty-two out of thirty-three panelists had sweat reduction of greater than 20%. Twenty-four hours after treatment of thirty-three panelists there was a cumulative average sweat reduction of 34% and twenty-eight out of thirty-three panelists had sweat reduction of greater than 20%.

Both the positive and negative controls behaved as expected, confirming that the experimental protocol was effective.

EXAMPLES II TO XI

Stability of Antiperspirant/Deodorant Sticks

One purpose for conducting the following stability tests was to illustrate that the low residue antiperspirant formulations of the invention have melting points comparable to those presently commercially available, i.e., (a) they must evidence a weight loss that is less than one percent by weight at a sustained temperature of 122 degrees F., and (b) they must also be able to maintain their original "shape".

Another purpose for conducting the tests was to illustrate the criticality of the ingredients considered essential to the invention as well as the amounts utilized thereof.

In the following tests, two sticks of each formulation were placed in an oven which was maintained at a temperature of about 122 degrees F. The residence time was three days. Each stick was pre-weighed, wrapped in paper towels and placed on their sides to simulate a stick in a suitcase or gym bag. After a period of three days each was cooled to room temperature, reweighed and the percentage weight loss was calculated.

EXAMPLE II

Sodium bicarbonate-containing antiperspirant sticks were prepared in a manner similar to Example I. The sticks which were employed as "standards" in subsequent comparative tests contained those ingredients deemed essential to the present invention as well as the amounts thereof. The ingredients and amounts utilized in the "standard" were as follows:

| INGREDIENTS | | | |
|---|---|---|---|
| Supplier | Trade Name | CTFA Name | Weight Percent |
| Dow | Dow 245 | Cyclomethicone | 31.00 |
| Van Dyk | Ceraphyl 230 | Diisopropyl adipate | 11.00 |
| P & G | C01895 | Stearyl alcohol | 20.00 |
| CasChem | Castorwax MP-70 | Hydrogenated castor oil | 3.00 |
| Degussa | Aerosil 200 | Fumed silica | 1.50 |
| Reheis | Rezal 36GP SUF | Aluminum zirconium tetrachlorohydrex glycine | 20.00 |
| Vista | Alfol 20+ Alcohol | Eicosanol | 0.50 |
| Church & Dwight | Baking Soda 3DC | Sodium Bicarbonate 3DC | 5.00 |
| Amerchol | Fluid AP | PPG 14 butyl Ether | 7.70 |
| — | Fragrance | — | 0.30 |
| | | | 100.00 |

The ratio of Cyclomethicone to Diisopropyl adipate was about 2.82:1.

The percentage weight loss was as follows:

Run No. 1=0.84

Run No. 2=0.70

The above weight losses were well below the level required for commercial acceptance.

The foregoing Examples illustrate the marked differences resulting when the ratio of cyclomethicone to diisopropyl adipate employed is outside the range of the present invention. Each run of Examples III to VIII is well above the target of one percent or less weight loss at prolonged periods of time at a temperature of about 122 degrees F.

The following Examples serve to illustrate that while the ratio of volatile silicone oil to water-insoluble liquid emollient is, according to the present invention, essentially greater than about 2.5:1, the use of such ratio is necessary because of the presence of a bicarbonate in the antiperspirant/deodorant stick formulation. Accordingly, the following Examples illustrate the effect of the utilization of a bicarbonate, i.e., sodium bicarbonate.

The following Examples illustrate the importance of using a ratio of volatile silicone oil to water-insoluble liquid emollient. The Examples below compare to use of ratios of about 1:1 with the ratio of slightly less than 3:1 which was utilized in Example II.

| INGREDIENTS (Wt %) | EXAMPLE NUMBER | | | | | | | | | | | |
|---|---|---|---|---|---|---|---|---|---|---|---|---|
| | II | III | IV | V | VI | VII | VIII | IX(a) | IX(b) | X(a) | X(b) | XI |
| Cyclomethicone | 31.00 | 20.00 | 19.00 | 19.00 | 20.50 | 22.00 | 21.00 | 36.70 | 36.70 | 15.00 | 15.00 | 42.45 |
| Diisopropyl adipate | 11.00 | 25.00 | 21.00 | 21.00 | 22.00 | 22.00 | 19.00 | 15.00 | 15.00 | 36.70 | 36.70 | 14.15 |
| Stearyl alcohol | 20.00 | 15.00 | 20.00 | 20.00 | 17.50 | 18.00 | 20.00 | 18.00 | 18.00 | 18.00 | 18.00 | 18.00 |
| Hydrogenated castor oil | 3.00 | 1.00 | 1.00 | 1.00 | 1.00 | 1.00 | 1.00 | 3.00 | 3.00 | 3.00 | 3.00 | 3.00 |
| Fumed Silica | 1.50 | 1.50 | 1.50 | 1.50 | 1.50 | 1.50 | 1.50 | 1.50 | 1.50 | 1.50 | 1.50 | 1.50 |
| Aluminum zirconium tetrachlorohydres glycine | 20.00 | 20.00 | 20.00 | 20.00 | 20.00 | 20.00 | 20.00 | 20.00 | 20.00 | 20.00 | 20.00 | 20.00 |
| Eicosanol | 0.50 | — | — | — | — | — | — | 0.50 | 0.50 | 0.50 | 0.50 | 0.50 |
| Sodium Bicarbonate | 5.00 | 5.00 | 5.00 | 5.00 | 5.00 | 5.00 | 5.00 | 5.00 | — | 5.00 | — | — |
| PPG 14 butyl Ether | 7.70 | 12.20 | 12.20 | 12.20 | 12.20 | 10.20 | 12.20 | — | — | — | — | 0.40 |
| Fragrance | 0.30 | 0.30 | 0.30 | 0.30 | 0.30 | 0.30 | 0.30 | 0.30 | 0.30 | 0.30 | 0.30 | 0.40 |
| | 100.00 | 100.00 | 100.00 | 100.00 | 100.00 | 100.00 | 100.00 | 100.00 | 100.00 | 100.00 | 100.00 | 100.00 |
| Ratio Cyclomethicone to Diisopropyl Adipate | 2.82:1 | 0.8:1 | 0.90:1 | 0.90:1 | 0.93:1 | 1:1 | 1.1:1 | 2.5:1 | 2.5:1 | 1:2.5 | 1:2.5 | 3:1 |
| Percentage Weight Loss | | | | | | | | | | | | |
| Run No. 1 | 0.84 | 14.56 | 6.80 | 5.44 | 7.98 | 9.46 | 7.98 | 1.08 | 0.19 | 5.76 | 0.52 | 0.14 |
| Run No. 2 | 0.70 | 10.43 | 7.51 | — | 9.05 | 8.17 | 7.43 | 1.04 | 0.07 | 6.05 | 0.48 | 0.12 |

Reference to the foregoing Examples indicates that a comparison of Example IX(a) with IX(b) shows that use of 5.0 weight percent sodium bicarbonate reduces the heat stability of the antiperspirant/deodorant stick greater than five-fold even though the ratio of volatile silicone to water-insoluble liquid emollient is according to the present invention. A comparison of Examples X(a) with X(b) illustrates that while a suitable heat stability can be obtained even with a ratio of silicone to liquid emollient outside the instant invention (e.g., 1:2.5 in Examples X(a) and X(b)) the use of 5.0 weight percent markedly reduces the desired heat stability (e.g., Example X(a), 5.76 amd 6.05 compared with a 0.52 and 0.48 in Example X(b)). Example XI shows that good heat stability can be obtained if no bicarbonate is employed.

A comparison of the following Examples illustrates that while the use of a water-insoluble liquid emollient, e.g., diisopropyl adipate, to improve product residue works extremely well, when combined with sodium bicarbonate, however, it causes the sticks to melt and leak out of their containers. Such phenomena is avoided, however, when a coupling agent, e.g., PPG14 butyl ether, is employed.

| INGREDIENTS (Wt. %) | EXAMPLE NUMBER | | | | |
|---|---|---|---|---|---|
| | II | XII | XIII | XIV | XV |
| Cyclomethicone | 31.00 | 44.95 | 43.95 | 44.95 | 24.85 |
| Disopropyl adipate | 11.00 | 12.15 | 11.15 | 12.15 | 24.85 |
| Stearyl alcohol | 20.00 | 15.00 | 14.00 | 15.00 | 20.00 |
| Hydrogenated castor oil | 3.00 | 1.00 | 1.00 | 1.00 | 3.00 |
| Fumed silica | 1.50 | 1.50 | 1.50 | 1.50 | 1.50 |
| Aluminum zirconium tetrachlorohydrex glycine | 20.00 | 20.00 | 20.00 | 20.00 | 20.00 |
| Eicosanol | 0.50 | — | — | — | 0.50 |
| Sodium Bicarbonate | 5.00 | 5.00 | 8.00 | 5.00 | 5.00 |
| PPG 14 butyl Ether | 7.70 | — | — | — | — |
| Fragrance | 0.30 | 0.40 | 0.40 | 0.40 | 0.30 |
| | 100.00 | 100.00 | 100.00 | 100.00 | 100.00 |
| Ratio Cyclomethicone to Diisopropyl adipate | 2.82:1 | 3.7:1 | 3.9:1 | 3.7:1 | 1:1 |
| Percentage Weight Loss | | | | | |
| Run No. 1 | 0.84 | 5.02 | 4.22 | 2.28 | 3.41 |
| Run No. 2 | 0.70 | 4.62 | 4.00 | 2.26 | 3.16 |

The foregoing Examples illustrate that formulations which are otherwise in accordance with the invention, i.e., Examples XII–XIV, do not exhibit suitable heat stability when the coupling agent, e.g.; PPG 14 butyl ether, is not employed. Example XV illustrates that changing the ratio of volatile silicone oil to water-insoluble liquid emollient does not improve heat stability, absent the use of a coupling agent.

Although the present invention has been described and illustrated with reference to specific examples, it is understood that modifications and variations of composition and procedure are contemplated within the scope of the following claims.

What is claimed is:

1. An antiperspirant stick which provides the user with excellent antiperspirant/deodorant efficacy, reduced residue and high temperature stability, which comprises
   (a) from about 25 to 50 percent by weight of a volatile silicone oil;
   (b) from about 2 to 20 percent by weight of a water-insoluble liquid emollient;
   characterized in that the weight ratio of volatile silicone oil to water-insoluble liquid emollient is from about 5.0:1 to 25.0:1
   (c) from about 12 to 20 percent by weight of a low melting point wax;
   (d) from about 1.0 to 15 percent by weight of a coupling agent;
   (e) from about 0.50 to 3.0 percent by weight of a surface active agent which is a non-ionic ether or ester having a HLB greater than about 10;
   (f) from about 18 to 30 percent by weight of an antiperspirant active material; and
   (g) from about 1.0 to 30 percent by weight of a sodium bicarbonate deodorant active material.

2. The antiperspirant stick of claim 1 wherein the volatile silicone oil is a cyclic or linear polydimethylsiloxane containing from about 3 to 9 silicon atoms.

3. The antiperspirant stick of claim 2 wherein the cyclic volatile polydimethylsiloxane has the following general formula:

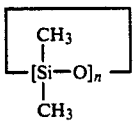

wherein n equals from about 3 to 7.

4. The antiperspirant stick of claim 3 wherein the cyclic volatile polydimethylsiloxane is cyclomethicone.

5. The antiperspirant stick of claim 2 wherein the linear polydimethylsiloxane contains from about 3 to 9 silicon atoms per molecule and has the following general formula:

$$(CH_3)_3Si-O[Si(CH_3)_2-O]_n-Si(CH_3)_3$$

wherein n equals from about 1 to 7.

6. The antiperspirant stick of claim 2 wherein the linear volatile silicone materials generally have viscosities of less than about 5 centistokes at 250° C. and the cyclic materials have viscosities of less than about 10 centistokes at 25° C.

7. The antiperspirant stick of claim 1 wherein the water-insoluble liquid emollient is a water-insoluble organic material which is in the liquid state at ambient temperature and has a water solubility of less than about 1% at 25 degrees C. and is selected from the group consisting of fatty acids, fatty alcohols, esters, alkanes, such silicones, and cyclic dimethyl polysiloxanes and ethers therefrom.

8. The antiperspirant stick of claim 7 wherein the water-insoluble liquid emollient is diisopropyl adipate.

9. The antiperspirant stick of claim 1 wherein the low melting point wax is characterized by having a melting point of from about 37 degrees C. to about 75 degrees C.

10. The antiperspirant stick of claim 1 wherein the low melting point wax comprises from about 15 to 19 percent by weight of the total weight of the stick composition.

11. The antiperspirant stick of claim 1 wherein the low melting point wax is selected from the group consisting of fatty acids, fatty alcohols, fatty acid esters, and fatty acid amides, having fatty chains of from about 8 to about 30 carbon atoms.

12. The antiperspirant stick of claim 1 wherein the low melting point wax is replaced with from about 0.5 to 5 percent by weight based on the total weight of the composition of a water-insoluble high melting point wax having a melting point of from about 65 degrees to 100 degrees C.

13. The antiperspirant stick of claim 12 wherein the high melting point wax is hydrodenated castor oil.

14. The antiperspirant stick of claim 1 wherein the coupling agent is selected from the group consisting of $C_6$-$C_{22}$ fatty alcohols, ethoxylated derivatives of $C_4$-$C_{22}$ fatty alcohols, and mixtures thereof.

15. The antiperspirant stick of claim 1 wherein the coupling agent comprises from about 6.5 to 10 percent by weight, based on the total weight of the stick composition.

16. The antiperspirant stick of claim 14 wherein the coupling agent is PPG-14 butyl ester.

17. The antiperspirant stick of claim 1 wherein the surface active agent is a polyethylene glycol distearate.

18. The antiperspirant stick of claim 1 wherein the antiperspirant active material is a coordination complex of aluminum zirconium tetrachlorohydrate (q.v.) and glycine (q.v.) in which some of the water molecules normally coordinated to the metals have been displaced by the glycine.

19. The antiperspirant stick of claim 1 wherein the antiperspirant active material comprises from about 20 to 24 percent by weight based on the total weight of the stick composition.

20. The antiperspirant stick of claim 1 wherein the sodium bicarbonate has an average particle size of from about 25 to 250 microns.

21. The antiperspirant stick of claim 1 wherein the deodorant active material comprises from about 0.05 to 10 percent, based on the total weight of the stick composition, of a bacteriostat in addition to sodium bicarbonate.

22. The antiperspirant stick of claim 21 wherein the bacteriostat is Triclosan.

23. The antiperspirant stick of claim 1 wherein the stick composition contains from 0 to about 4 percent by weight of a particulate suspending material.

24. The antiperspirant stick of claim 23 wherein the particulate suspending material is fumed silica.

25. A method for preventing and controlling perspiration wetness in humans comprising the application to the underarm area of an effective amount of the suspensoid low residue antiperspirant stick composition according to claim 1.

26. A method for treating or preventing underarm malodor associated with human perspiration, said method comprising applying to the skin of a human a safe and effective amount of cosmetic stick composition according to claim 1.

* * * * *